United States Patent [19]
Benderev et al.

[11] Patent Number: 5,938,686
[45] Date of Patent: *Aug. 17, 1999

[54] METHOD OF INSTALLING BONE ANCHOR

[75] Inventors: Theodore V. Benderev, Laguna Hills; Neil H. Naves; Mark J. Legome, both of Mission Viejo; Sheila Wallin, Laguna Beach, all of Calif.

[73] Assignee: Boston Scientific Technology, Inc., Maple Grove, Minn.

[ * ] Notice: This patent is subject to a terminal disclaimer.

[21] Appl. No.: 08/887,241

[22] Filed: Jul. 2, 1997

Related U.S. Application Data

[63] Continuation of application No. 08/385,897, Feb. 9, 1995, Pat. No. 5,766,221, which is a continuation-in-part of application No. 08/042,739, Apr. 5, 1993, Pat. No. 5,611,515, which is a continuation-in-part of application No. 07/862,847, Apr. 3, 1992, abandoned, which is a continuation-in-part of application No. 07/801,747, Dec. 3, 1991, abandoned.

[51] Int. Cl.⁶ .................................................. A61B 17/00
[52] U.S. Cl. .............................. 606/232; 606/73; 606/96; 606/104; 128/898
[58] Field of Search .............................. 606/72, 73, 75, 606/104, 232, 96; 128/898

[56] References Cited

U.S. PATENT DOCUMENTS

| | | |
|---|---|---|
| 1,030,530 | 6/1912 | Palmer . |
| 2,200,120 | 5/1940 | Nauth . |
| 2,400,251 | 5/1946 | Nagel . |
| 2,454,680 | 11/1948 | Stephens . |
| 2,666,430 | 1/1954 | Gispert . |
| 2,707,783 | 5/1955 | Sullivan . |
| 2,738,790 | 3/1956 | Todt, Sr. et al. . |
| 2,809,628 | 10/1957 | Joseph . |
| 3,669,118 | 6/1972 | Colon-Morales . |
| 3,835,849 | 9/1974 | McGuire . |
| 3,842,825 | 10/1974 | Wagner . |
| 3,892,232 | 7/1975 | Neufeld .................................. 606/80 |
| 3,995,619 | 12/1976 | Glatzer . |
| 4,156,424 | 5/1979 | Burgin . |
| 4,172,458 | 10/1979 | Pereyra . |
| 4,257,411 | 3/1981 | Cho . |
| 4,323,057 | 4/1982 | Jamieson . |
| 4,325,373 | 4/1982 | Slivenko et al. . |
| 4,383,527 | 5/1983 | Asnis et al. . |

(List continued on next page.)

FOREIGN PATENT DOCUMENTS

| | | |
|---|---|---|
| 389 044 | 10/1989 | Austria . |
| 1 448 111 | 9/1976 | European Pat. Off. . |
| 0 059 044 | 9/1982 | European Pat. Off. . |
| 0 153 831 A3 | 9/1985 | European Pat. Off. . |
| 0 241 240 | 10/1987 | European Pat. Off. . |
| 0 281 763 A2 | 9/1988 | European Pat. Off. . |
| 0 440 991 A1 | 8/1991 | European Pat. Off. . |
| WO 92/00773 | 1/1992 | European Pat. Off. . |
| WO 93/10715 | 6/1993 | European Pat. Off. . |
| 0 558 993 A2 | 9/1993 | European Pat. Off. . |

(List continued on next page.)

OTHER PUBLICATIONS

M.S. Henderson, M.D., Bone Surgery Instruments, Mueller & Co. catalog, p. 7, Nov. 4, 1937.

Theodore V. Benderev, *A Modified Percutaneous Outpatient Bladder Neck Suspension System,* Journal of Urology 152:2316–2320, 1994.

Theodore V. Benderev, *Anchor Fixation and Other Modifications of Endoscopic Bladder Neck Suspension,* Urology, vol. 5, No. 5, 1992.

Ruben F. Gittes and Kevin R. Loughlin, *No–Incision Pubovaginal Suspension for Stress Incontinence,* Journal of Urology, 138:568–570.

(List continued on next page.)

*Primary Examiner*—Michael Buiz
*Assistant Examiner*—David O. Reip
*Attorney, Agent, or Firm*—Testa, Hurwitz & Thibeault, LLP

[57] ABSTRACT

A bone anchor implantation device is positioned over a bone, and a bone anchor is installed in a bone.

5 Claims, 10 Drawing Sheets

U.S. PATENT DOCUMENTS

| | | | |
|---|---|---|---|
| 4,421,112 | 12/1983 | Mains et al. . | |
| 4,527,726 | 7/1985 | Assell et al. | 227/19 |
| 4,535,768 | 8/1985 | Hourahane et al. . | |
| 4,545,374 | 10/1985 | Jacobson . | |
| 4,632,100 | 12/1986 | Somers et al. . | |
| 4,672,957 | 6/1987 | Hourahane . | |
| 4,686,972 | 8/1987 | Kurland . | |
| 4,708,139 | 11/1987 | Dunbar, IV . | |
| 4,713,077 | 12/1987 | Small | 623/16 |
| 4,722,331 | 2/1988 | Fox . | |
| 4,739,751 | 4/1988 | Sapega et al. . | |
| 4,744,353 | 5/1988 | McFarland . | |
| 4,784,126 | 11/1988 | Hourahane . | |
| 4,788,970 | 12/1988 | Kara et al. . | |
| 4,872,451 | 10/1989 | Moore et al. . | |
| 4,883,048 | 11/1989 | Purnell et al. . | |
| 4,898,156 | 2/1990 | Gatturna et al. | 606/72 |
| 4,899,743 | 2/1990 | Nicholson et al. | 606/139 |
| 4,911,153 | 3/1990 | Border | 606/98 |
| 4,920,958 | 5/1990 | Walt et al. | 606/96 |
| 4,938,760 | 7/1990 | Burton et al. | 600/29 |
| 4,945,904 | 8/1990 | Bolton et al. | 606/96 |
| 4,957,498 | 9/1990 | Caspari et al. | 606/146 |
| 4,978,351 | 12/1990 | Rozas | 606/98 |
| 4,985,032 | 1/1991 | Goble | 606/96 |
| 4,997,434 | 3/1991 | Seedhom et al. | 606/80 |
| 5,012,822 | 5/1991 | Schwarz | 128/885 |
| 5,013,292 | 5/1991 | Lemay | 600/30 |
| 5,026,376 | 6/1991 | Greenberg | 606/96 |
| 5,027,793 | 7/1991 | Engelhardt et al. . | |
| 5,030,219 | 7/1991 | Matsen, III et al. | 606/53 |
| 5,037,422 | 8/1991 | Hayhurst et al. | 606/72 |
| 5,061,181 | 10/1991 | Niznick | 433/174 |
| 5,108,397 | 4/1992 | White | 606/60 |
| 5,112,337 | 5/1992 | Paulos et al. | 606/96 |
| 5,112,344 | 5/1992 | Petros | 606/144 |
| 5,116,338 | 5/1992 | Poggie et al. | 606/90 |
| 5,141,513 | 8/1992 | Fortune et al. | 606/96 |
| 5,152,764 | 10/1992 | Goble | 606/96 |
| 5,152,765 | 10/1992 | Ross et al. | 606/99 |
| 5,156,616 | 10/1992 | Meadows et al. | 606/232 |
| 5,163,940 | 11/1992 | Bourque | 606/96 |
| 5,180,388 | 1/1993 | DiCarlo | 623/16 |
| 5,203,784 | 4/1993 | Ross et al. | 606/104 |
| 5,207,679 | 5/1993 | Li | 606/72 |
| 5,207,753 | 5/1993 | Badrinath | 606/96 |
| 5,217,486 | 6/1993 | Rice et al. | 606/232 |
| 5,224,946 | 7/1993 | Hayhurst et al. | 606/72 |
| 5,256,133 | 10/1993 | Spitz | 600/29 |
| 5,328,077 | 7/1994 | Lou | 227/175 |
| 5,370,662 | 12/1994 | Stone et al. | 606/232 |
| 5,372,146 | 12/1994 | Branch | 128/898 |
| 5,411,506 | 5/1995 | Goble et al. | 606/104 |
| 5,441,502 | 8/1995 | Bartlett | 606/104 |
| 5,443,482 | 8/1995 | Stone et al. | 606/232 |
| 5,520,700 | 5/1996 | Beyar et al. | 606/139 |
| 5,569,264 | 10/1996 | Tamminmaki et al. | 606/104 |
| 5,611,515 | 3/1997 | Benderev | 128/898 |

FOREIGN PATENT DOCUMENTS

| | | |
|---|---|---|
| WO 93/19678 | 10/1993 | European Pat. Off. . |
| 0 599 772 A1 | 6/1994 | European Pat. Off. . |
| 2 552 655 A1 | 4/1985 | France . |
| 2305815 | 8/1974 | Germany . |
| 2830566 | 1/1980 | Germany . |
| 29 07 962 A1 | 7/1980 | Germany . |
| 3412362 C1 | 10/1985 | Germany . |
| 1090377 | 5/1984 | Russian Federation . |
| 1225547 | 4/1986 | Russian Federation . |
| 2 069 846 | 9/1981 | United Kingdom . |
| 2 252 732 | 8/1992 | United Kingdom . |

OTHER PUBLICATIONS

George D. Webster, *Urologic Surgery, 3rd. Edition,* "Female Urinary Incontinance" Chapter 66, pp. 665–679.

M.S. Henderson, M.D., *For Treatment of the Neck of the Femur.*

Gary E. Leach, M.D., *Bone Fixation Technique for Transvaginal Needle Suspension,* Urology, 1988, XXXI:5, 388.

Kevin R. Loughlin, Willet F. Whitmore, III, Ruben F. Gittes, and Jerome P. Richie, *Review of an 8–year Experience with Modifications of Endoscopic Suspension of the Bladder Neck for Female Stress Urinary Incontinence,* Journal of Urology, 1989, 143:44–45.

Velenzio C. Mascio, M.D., *Therapy of Urinary Stress Incontinence In Women,* GII Anchor Systems.

Edward J. McGuire, M.D., *The Sling Procedure for Urinary Stress Incontinence,* Profiles in Urology.

Charles F. McKiel, Jr., Edwin C. Graf, and Daniel H. Callahan, *Marshall–Marchetti Procedure: Modification,* Journal of Urology, 96:737–739.

R.O. Parra and L. Shaker, *Experience with a Simplified Technique for the Treatment of Female Stress Urinary Incontinence,* Journal of Urology, (1990) 66:615–617.

Armand J. Pereyra, M. D., *A Simplified Surgical Procedure for the Correction of Stress Incontinence in Women,* West. J. Surg., Obst. & Gynec., 223–226.

Shlomo Raz, M.D., *Modified Bladder Neck Suspension for Female Stress Incontinence,* Journal of Urology, XVII:82–85.

Steven A. Scheuer, M.D., *The Modified Pereyra Bladder Neck Suspension Procedure,* GII Anchor Systems.

Steven, A. Scherer M.D., Mtek Modified Pereyra BNS (Videotape).

Julia R. Spencer, Vincent J. O'Connor, Jr., and Anthony J. Schaeffer, *A Comparison of Endoscopic Suspension of the Vesical Neck with Suprapubic Vesicourethropexy for Treatment of Stress Urinary Incontinence,* Journal of Urology, 137411–414.

Thomas A. Stamey, M.D., *Endoscopic Suspension of the Vesical Neck for Urinary Incontinence,* Surgery, Gynecology & Obstetrics, (1973) 136:547–554.

Chester C. Winter, M.D., *Peripubic Urethropexy for Urinary Stress Incontinence in Women,* Journal of Urology, (1982) XX:408–411.

GII Anchor System, Bladder Neck Suspension for Needle Suspension Techniques.

Bladder Neck Suspension Treatment of Female Stress Urinary (*Videotape*).

Vesica Medical—Percutaneous Bladder Neck Suspension (*Videotape*).

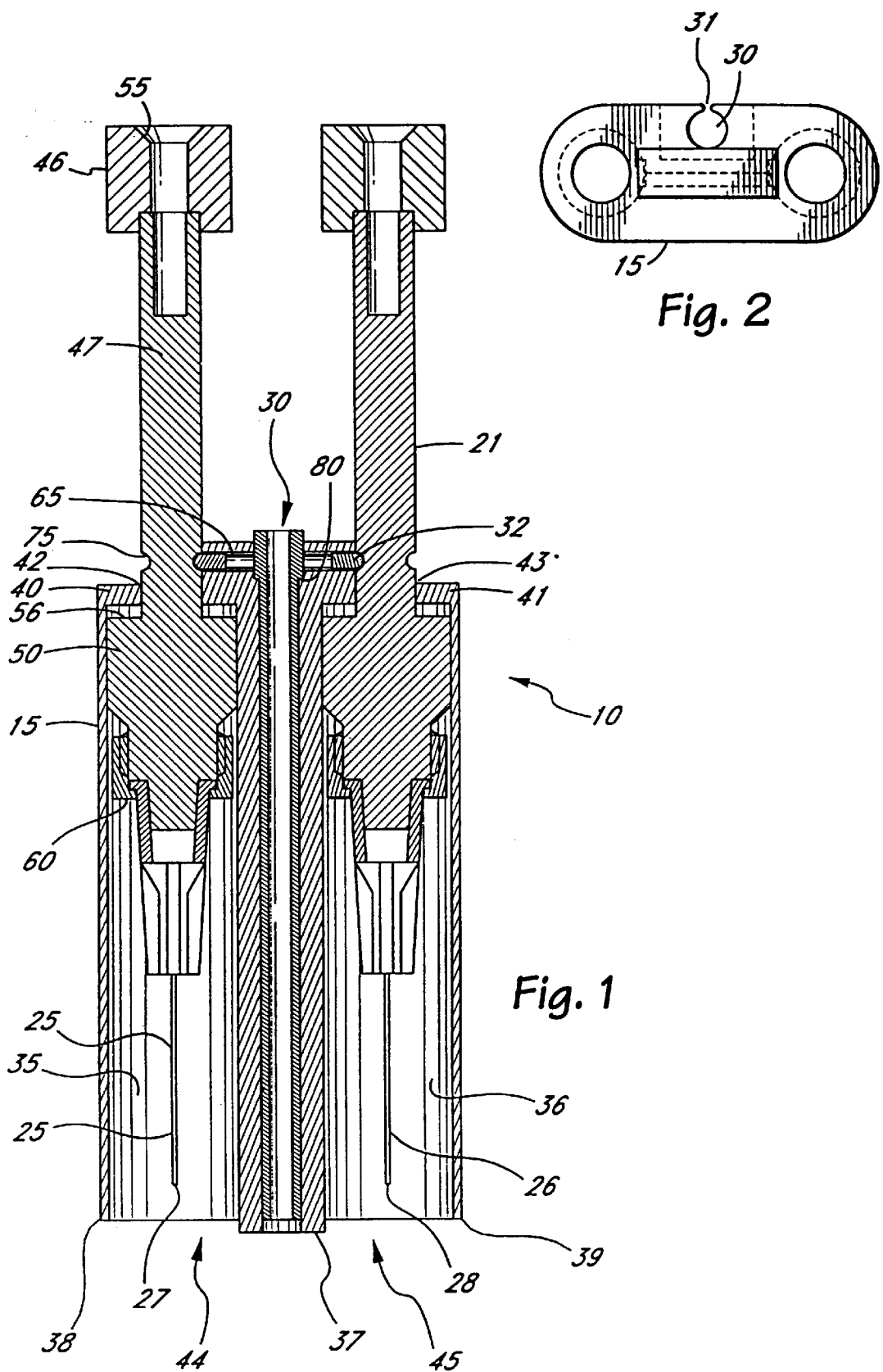

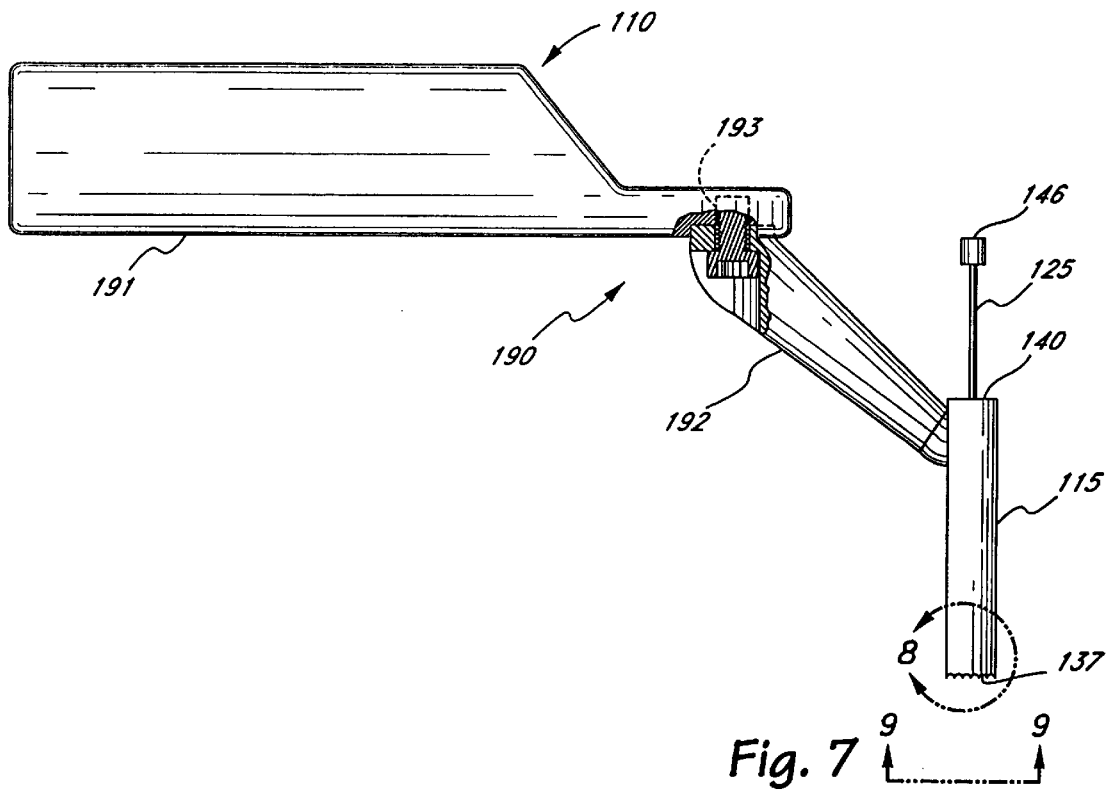
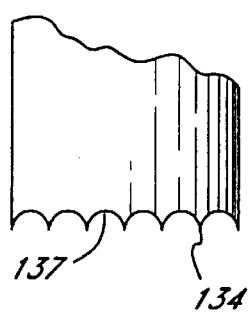
Fig. 8
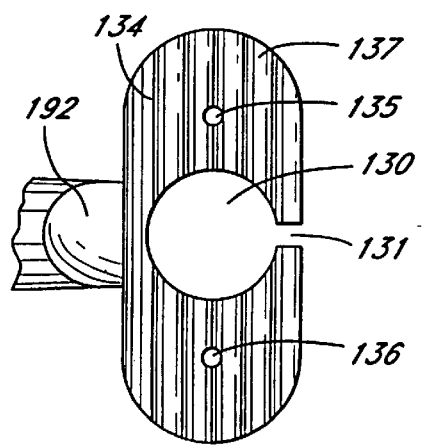
Fig. 9

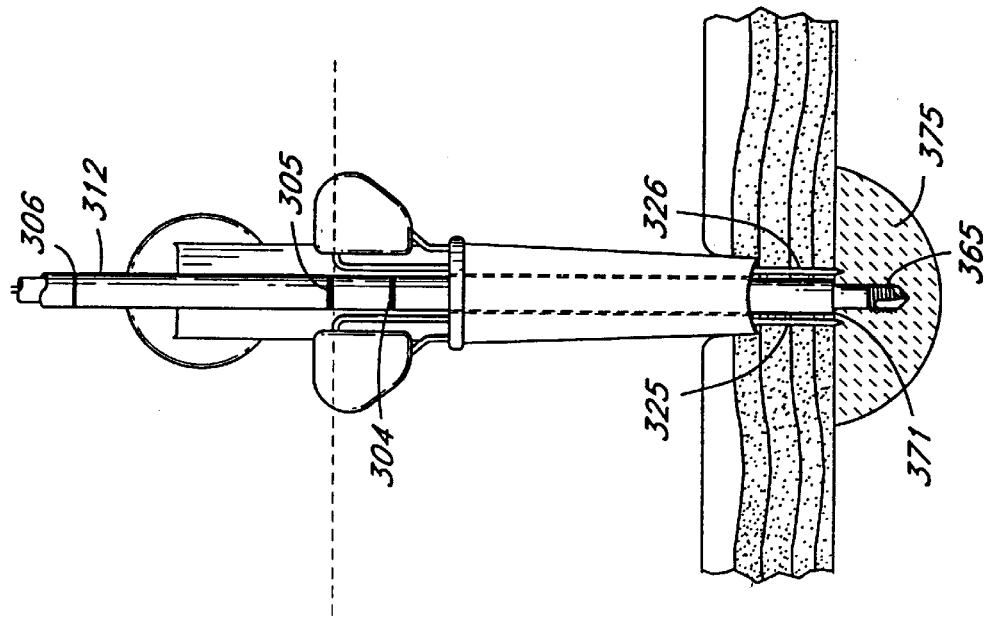

METHOD OF INSTALLING BONE ANCHOR

This application is a continuation of Ser. No. 08/385,897, filed Feb. 9, 1995, now U.S. Pat. No. 5,766,221; which is a continuation-in-part of Ser. No. 08/042,739, filed Apr. 5, 1993, now U.S. Pat. No. 5,611,515; which is a continuation-in-part of Ser. No. 07/862,847, filed April 3, 1992, now abandoned; which is a continuation-in-part of Ser. No. 07/801,747, filed Dec. 3 1991, now abandoned.

BACKGROUND OF THE INVENTION

The present invention relates to the treatment of stress urinary incontinence "SUI" and, in particular, to improved methods and surgical devices for the surgical treatment of SUI in females. The devices disclosed herein are additionally useful in a wide variety of other surgical procedures.

Genuine stress incontinence is the involuntary loss of urine due to a sudden rise in intra-abdominal pressure. It has been estimated that between 40% and 50% of young, healthy nulliparous women admit to occasional mild stress incontinence; however, at least 80% of stress incontinence patients are in the perimenopausal age group and are multiparous. Raz[3] has suggested that the female urethral continence mechanism is dependent on the interaction of four urethral factor: urethral closing pressure, urethral length, urethrotrigonal anatomy, and urethral reception of intra-abdominal pressure.

The urethral closing pressure is predominantly a result of the interaction of smooth and striated muscle sphincter activity, but there is also some contribution by nonmuscular urethral factors such as the submucosal vascular plexus, the elastin and collagen content of the urethral tissues, and a sphincter like effect of the mucosa. There has been considerable diversity of opinion regarding the anatomy structure and the innervation of the urethral sphincters, and a variety of views have been expressed in the literature.

Lapides and associates have stressed the importance of urethral length in the maintenance of continence in the female. However, although it certainly interacts with other factors to contribute to continence, a short urethra alone will not produce incontinence. Urethral length varies considerably in normal women, and women with proven genuine stress urinary incontinence do not invariably have urethral shortening.

Urethrotrigonal anatomy, which can be demonstrated by lateral cystourethrography, should fulfill certain criteria. The bladder base should lie above the level of the inferior ramus of the symphysis, and with straining should not descend more than 1.5 cm. There should be a normal urethrotrigonal alignment with an angle normally less than 100 degrees, and the urethral axis should be approximately 35 degrees from thevertical. In the hypermobile situation loss of all of the normal anatomic features may occur, a radiologic finding that correlates with the clinical finding of cystourethrocele. However, clinical experience has shown that the coexistence of cystourethrocele and incontinence does not predict that the incontinence is of a genuine stress variety.

The transmission of intra-abdominal pressure to the intra-abdominal portion of the proximal urethra is also reported to be important in the maintenance of continence. This is a passive phenomenon, and is the result of the normal anatomic configuration just described. Whenever there is a rise in intra-abdominal pressure during such stresses as coughing or straining, the pressure is transmitted not only to the bladder but also to the proximal urethra, with resultant increase in the closing pressure, and prevention of leakage. If the urethral axis is altered, rotational descent will drop the proximal urethra and bladder base from its intra-abdominal location, and will obviously impair such pressure transmission.

A wide variety of operations have been used to correct this condition, generally involving the principles of elevating the bladder neck anteriorly and/or elongating and narrowing the proximal urethra. Two of the most popular operations today for female stress incontinence are the Marshall-Marchetti-Krantz and Birch vesicourethropexies. The Marshall-Marchetti-Krantz technique has at least an eighty-five percent success rate, against which other operative success rates must be measured. Recently, the Pereyra operation and its modifications have enjoyed some popularity, but less than basic techniques.

Notwithstanding the foregoing, however, there remains a need for an improved treatment for SUI. Preferably, the treatment is as noninvasive as possible under the circumstances, and will eliminate or minimize hospitalization and the use of general anesthetics. In addition, there remains a need for improved medical instrumentation such as drill guides and suture passers for use in connection with SUI treatment and other medical procedures.

SUMMARY OF THE INVENTION

There is provided in accordance with one aspect of the present invention a bone anchor implantation device for directing a bone anchor at a selected site on a bone. The bone anchor implantation device includes a housing, at least two probes on the housing, and a guide channel extending through the housing. The guide channel lies on a plane which extends in between the probes. In one embodiment, the longitudinal axis of the guide channel is approximately equidistant from the longitudinal axes of each of the probes. The bone anchor implantation device also includes an anchor driver for axially advancing the bone anchor through the guide channel and into the bone. The anchor driver has visual indicia for indicating the axial position of the bone anchor relative to the bone. The relative depth of the bone anchor is indicated when the indicia on the anchor driver is aligned with reference indicia on the probes or the housing. Optionally, the visual indicia on the anchor driver is a mark. Optionally the reference is a proximal portion of at least one of the probes. When the indicia on the anchor driver is a mark, the location of the mark and the reference indicia are such that when the driver is advanced sufficiently distally to bring the mark and the reference indicia into alignment, and the first and second probes are in contact with the bone, the bone anchor is at an installed depth within the bone. In one embodiment, the probes are axially movable from a first proximal position to a second distal position. When the probe is in the first position, the distal tip is shielded within the housing. When the probe is in the second position, the distal tip is exposed outside of the housing. The probe can be an elongate solid wire. In one embodiment, the probes have sufficient axial integrity to penetrate a bone so that the housing is maintained in a stable position.

In accordance with another aspect of the present invention, there is provided an alternate embodiment of the bone anchor implantation device for use in positioning a bone anchor in a bone. The bone anchor implantation device includes a housing, at least one probe mounted to the housing, a guide channel extending through the housing, and an anchor driver. The anchor driver is axially movably received within the guide channel for advancing a bone anchor through the guide channel. The anchor driver has visual indicia for indicating the position of the bone anchor relative to the distal end of the probe. The probe can be axially movably disposed within a probe channel on the housing. The probe can also be axially movably disposed within the guide channel. The distal end of the housing can be provided with a tissue contacting surface. The tissue contacting surface can be concave for complementary receipt of the soft tissue overlying the bone in which the bone anchor is to be placed. In addition, the tissue contacting surface can have a plurality of serrations for gripping the underlying tissue. In a two-probe embodiment, the longitudinal axes of the two probes are separated by a distance within the range of from about 5 millimeters to about 20 millimeters.

In accordance with another aspect of the present invention, there is provided an alternate embodiment of a bone anchor implantation device for directing a bone anchor at a selected site in order to introduce the bone anchor through tissue and into the bone. The bone anchor implantation device includes a housing, at least one probe slidably extendable through the housing, a guide channel extending through the housing, and an anchor driver for passing through the guide channel. The anchor driver is provided with visual indicia for indicating the position of the bone anchor relative to the bone. A first visual indicia on the anchor driver indicates that the bone anchor is in contact with the surface of the bone. A second visual indicia on the anchor driver indicates the bone anchor is at an implanted depth within the bone.

In accordance with a further aspect of the present invention, there is provided a method of installing a bone anchor in a bone. The method includes providing a bone anchor implantation device of the type having at least one axially extending bone probe and a guide channel extending therethrough. The bone probe is positioned such that the distal end of the probe is in contact with the bone. Also provided is an anchor driver having a bone anchor on its distal end. The anchor driver is advanced through the guide channel to position the bone anchor in the bone. After the bone anchor is positioned in the bone, the anchor driver is withdrawn from the guide channel, leaving the anchor in the bone. In one embodiment, the advancing step includes advancing the driver until the visual indicia on the driver indicate that the anchor has reached a predetermined installed depth in the bone. Optionally, the advancing step includes rotating the anchor driver.

BRIEF DESCRIPTION OF THE DRAWINGS

FIG. 1 is an elevational partial cross sectional schematic view of a drill guide and bone anchor implantation device in accordance with the present invention.

FIG. 2 is an end view of the drill guide of FIG. 1.

FIG. 7 is a side view with a partial cross section of the drill guide of FIG. 5.

FIG. 8 is an enlarged side view of the end of the drill guide of FIG. 7.

FIG. 9 is an enlarged end view of the drill guide of FIG. 7.

FIG. 15 is a front elevational view of an alternate embodiment bone anchor implantation device of the present invention with the anchor driver in a first position.

FIG. 16 is a view as in FIG. 15 with the anchor driver in a second position.

DETAILED DESCRIPTION OF PREFERRED EMBODIMENTS

Figure 3:
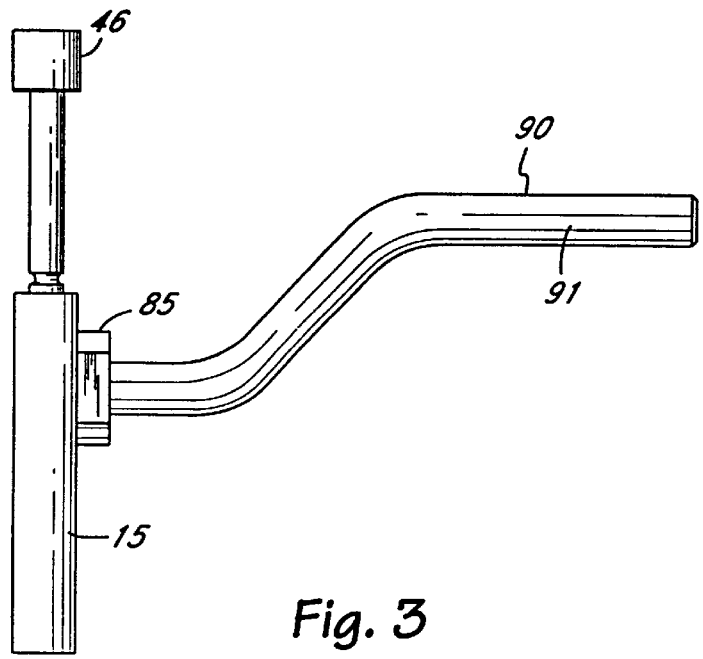
FIG. 3 is a side elevational schematic view of the drill guide of FIG. 1.
Figure 4:
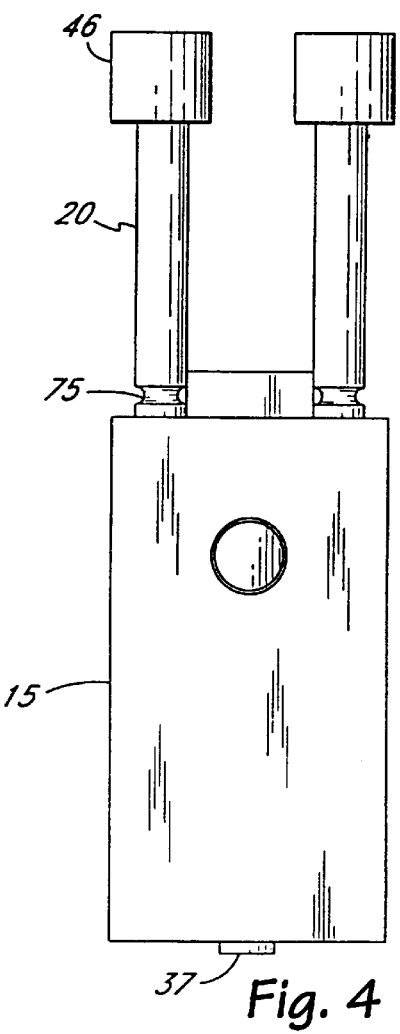
FIG. 4 is a front elevational view of the drill guide shown in FIG. 3.

SUI is generally curable with any of a variety of surgical procedures that properly suspends the bladder neck. However, limitations of known procedures include (1) the extent of surgical morbidity, (2) the ever-present threat of long term failures, and (3) the reproducibility between different surgeons.

Pereyra[1] introduced the transvaginal bladder neck suspension as a less invasive alternative to open retropubic procedures. Stamey[2] limited morbidity and improved the reproducibility of the transvaginal bladder neck suspension by introducing endoscopic control and confirmation of suture placement. Raz[3] has improved reproducibility by introducing full palpatory control of needle passage through the retropubic space, thereby limiting disability through injury to the bladder or other retropubic structures.

The distal passage of the suture passer disclosed in copending U.S. application Ser. No. 08/078,730, filed Jun. 17, 1993 now U.S. Pat. No. 5,439,467, which is incorporated herein by reference, or other needle followed by a sweep back to the bladder neck area described in copending U.S. application Ser. No. 08/042,739, filed Apr. 5, 1993 now U.S. Pat. No. 5,611,515, which is incorporated herein by reference, accomplishes a similar goal but without the necessity of entering the retropubic space. Passage of the needle point to the level of the introitus along the underside of the pubic bone obviates the need to turn the needle down toward a bladder neck that has been digitally elevated, thereby reducing the risk of bladder injury. Extraction of the needle from the pubourethral ligament is necessary to allow a "capture" of the more pliable pubocervical fascia alongside the urethra. The subsequent, gentle sweep back of the needle along the surface of the pubocervical fascia provides an easy and safe means of introducing the needle to the bladder neck area under the vaginal digital guidance.

Gittes and Loughlin[5] have further popularized the technique of Pereyra and demonstrated an advantage of increased long-term efficacy by creating an autologous bolster with the transvaginal passage of a curved needle. As an alternative manner of creating an autologous bolster, the proposed modification described in copending U.S. application Ser. No. 08/042,739, filed Apr. 5, 1993 now U.S. Pat. No. 5,611,515, which is incorporated herein by reference, uses the suture passer disclosed in copending U.S. application Ser. No. 08/078,730, filed Jun. 17, 1993 now U.S. Pat. No. 5,439,467, which is incorporated herein by reference, or a Stamey needle through a suprapubic approach to carry the suture through all of its vaginal passes. The full carriage of the suture by the suture passer needle offers the benefits of (1) improving accuracy and reproducibility by allowing palpation of the needle at each vaginal entry point in reference to the bladder neck and catheter, (2) potentially decreasing morbidity by reducing the risk of injury and/or irritation through inadvertent entry into any part of the urethra or bladder, and (3) possibly contributing to long term efficacy by assuring that a full thickness layer of pubocervical fascia is captured. This technique permits the capture of a large lateral volume of pubocervical fascia similar in an area to that available for suturing in an open retropubic urethropexy.

Leach[4] has limited morbidity by decreasing postoperative pain and has potentially improved long-term efficacy with pubic fixation of the suspending sutures. However, the trochar needle passage through the pubic bone as described by Leach can be difficult through the limited exposure that is used with some forms of endoscopic bladder neck suspension. Other various forms of pubic bone fixation have also been described with transvaginal and open bladder neck suspension surgery[6,7,8]. To facilitate the anchoring of the suspensory suture to the pubic bone with minimal soft tissue dissection, the present inventor has developed new methods and apparatus for anchoring the suture. The present invention contemplates any of a variety of bone anchors, including the Mitek Anchor System. The latest generation of Mitek anchor, the G2, consists of a titanium body coupled to nickel-titanium arcs. These anchors have recently been used most commonly for tenodesis and ligamentous reconstruction of the shoulder and foot[9,10].

In the present setting of bladder neck suspensions, the Mitek anchor with attached suture is passed into a hole drilled in the pubic bone. Care must be taken to assure that the hole has been drilled into the pubic bone and not inferiorly through the tendon of the adductor longus or superiorly through the rectus fascia over the surface of the pubis. Proper location of the drill and placement of the bone anchor in the bone is facilitated by the drill guide illustrated in FIGS. 1–4 and discussed infra.

Once the anchor is passed into the bone, the anchor's unique memory forces the arcs to spring open to their original shape and to engage in the cancellous portion of the pubic bone. The complication of infection with use of the anchor has not been noted, which may, in part, be due to the emphasis on broad spectrum antibiotics and sterile technique with use of video endoscopy, when possible.

Anchor pubic bone fixation in one study by the inventor, described in copending U.S. application Ser. No. 08/042,739, filed Apr. 5, 1993 now U.S. Pat. No. 5,611,515, which is incorporated herein by reference, was associated with a limitation of postoperative pain allowing the procedure to be performed on an outpatient basis in many of the patients. Pubic anchor fixation may limit suspending suture pull through at the level of the rectus fascia. Any assessment of resultant improvement of long term efficacy will require longer follow-up.

In accordance with one aspect of the present invention, there is provided a drill guide for locating drill sites inside a patient's body. More specifically, the invention relates to a multi-probe bone locator and drill guide centering device for locating a desired site on a bone, guiding a drill bit to the located site, retaining access to the site following drilling, and installation of a bone anchor for anchoring sutures.

Referring to FIG. 1, there is shown a surgical drill guide and/or a bone anchor implantation device 10 in accordance with one aspect of the invention. Generally, drill guide 10 comprises a body 15 carrying two or more plungers 20, 21, each having a bone probe 25, 26 at its end. A guide shaft 30 is located between two adjacent bone probes 25, 26. Alternatively, one or more of the plungers 20, 21 can be eliminated, so that one or more probes 25, 26 is directly mounted within or to body 15. Thus, in a simplified design, a drill guide channel is held in proximity to two or more elongate probes such as hypodermic needles which are preferably axially movable.

Body 15 is the support structure for the drill guide 10. The body 15 may have any of a variety of exterior configurations; however, it is preferred that the body be sufficiently axially elongate to facilitate withdrawal of the sharpened distal tips 27, 28 of the probes 25, 26 therein to minimize accidental needle sticks, and generally oval or rectangular in cross section. See, e.g., FIG. 2. The inside of the body 15 has two or more identical chambers 35, 36 spaced apart from each other to accommodate a drill guide shaft 30, as will be discussed. Preferably, an annular tissue compression portion 37 of body 15 adjacent the guide shaft 30 extends slightly farther in the distal direction than the lateral sidewalls 38, 39 of the body 15. Tissue compression portion 37 is optimally provided with a rough or serrated edge surface for contacting the tissue surrounding the drill site as will be discussed.

Each chamber 35, 36 extends from the distal end of the body 15 to a point near the proximal end of the body 15. In this manner, chambers 35, 36 are provided with open distal ends to permit reciprocal axial motion of the bone probes 25, 26 therethrough. Proximal ends of chambers 35, 36 are provided with a stop such as end walls 40, 41 having central passageways 42, 43 therethrough for movably accepting the plungers 20, 21. Similarly, distal ends 44, 45 of chambers 35, 36 can be provided with an end wall (not illustrated) having a probe opening therein, or a pierceable septum for permitting passage of probes 25, 26 therethrough.

The exact distance between the axes of adjacent chambers 35, 36 depends on the procedure for which the device is to be used. For example, in a bladder neck suspension procedure, the axes of chambers 35 should be separated by a distance of no more than about 10 mm from their centerlines, in an embodiment having coaxial probes and plungers, so that the corresponding probe separation is also no more than about 10 mm. Preferably, the separation between adjacent probes is within the range of from about 5 mm to about 15 mm.

Due to the bilateral symmetry of the illustrated embodiment, only one side will be particularly described below. The plunger 20 preferably comprises three main portions: an engaging knob 46, a main shaft 47 and a stop 50. The knob 46 is generally a cylindrical body attached to the top of the shaft 47 and shaped for easy engagement with a thumb or hand. This knob 46 may be attached to shaft 47 in a variety of manners. For example, knob 46 is illustrated as having a recessed portion on its distal surface for accepting the proximal end of shaft 47. A screw 55, preferably flat headed, is then passed through the top of the knob into the top of the shaft 47 to securely lock them together. Alternatively, the shaft 47, knob 46 and stop 50 can be integrally molded from any of a variety of thermoplastic materials well known in the art of surgical instrument manufacturing.

The plunger shaft 47 extends from the knob 46 through the opening 42. in the proximal end wall 40 of the body 15 and into chamber 35. Shaft 47 preferably is at least about 25 mm long from the distal surface of the knob 46 to the proximal surface of end wall 40 on body 15. In this manner, the plungers 20, 21 have a sufficient range of axial travel between a first, retracted position in which the distal tips 27, 28 of probes 25, 26 are shielded, and a second, extended position in which the distal tips 27, 28 of probes 25, 26 are exposed. It is contemplated, however, that the length of the shaft 47, probe 25 and axial travel may vary depending on the intended procedure.

A stop 50 is positioned on the distal end of the shaft 47. The stop 50 and shaft 47 may either be separately fabricated or may be fashioned from one piece of material such as by known molding or lathing techniques. The illustrated stop 50 comprises a radially outwardly extending portion of the plunger 20 which travels within the chamber 35 to produce a transverse abutment surface 56. The stop 50 thus limits the proximal range of travel of the plunger 20 by engagement of the abutment surface 56 with the distal surface of end wall 40 of the body 15. The stop 50 is preferably provided at its distal end with a connector such as a standard luer for attachment of a probe 25. As will be appreciated by one of skill in the art, any of a wide variety of interlocking or complementary surface structures can be devised to accomplish the function of stop 50.

In the illustrated embodiment, the probe 25 is inserted into a threaded cap 60. This cap 60 is preferably threaded on its interior surface so that it may be attached to the correspondingly threaded distal end of stop 50. Alternatively, the probe 25 can be connected to the stop 50 or shaft 47 such as by molding the proximal end of the probe 25 therein.

Each probe 25, 26 extends from the corresponding shaft 47 towards the distal end of the chamber 35. Probe 25 may comprise standard hypodermic tubing such as a standard needle, or a solid wire probe preferably having a sharpened distal end.

The length of the probe 25 is preferably such that when the plunger 20 is in a fully retracted state, the distal end of the probe 25 is spaced by at least about 4 mm from the open distal end of the chamber 35. In this manner, the probe end is protected against contamination and the user of the drill guide 10 is protected against accidental probe sticks. Alternatively, the probes 25, 26 can be rigidly secured to the body 15 or directly to a tubular drill guide shaft 30 as will be apparent to one of skill in the art.

In an embodiment having axially movable plungers, the plunger 20 is normally retracted proximally such that the distal tip 27 of probe 25 connected thereto is recessed from the distal end 44 of the chamber 35. This position is preferably releasably maintained by engaging rods 65 which are biased in the direction of annular recess 75 in the shaft 47 of the plunger 20.

In the illustrated embodiment, annular recess 75 is provided in the plunger shaft 47 at a point adjacent the proximal end of the body 15. When the plunger 20 is retracted, recess 75 releasably receives rod 65. This rod 65 is biased such as by a spring so that it provides an interference fit within recess 75 and holds the plungers 20 in their retracted position. The rods 65 and springs are preferably mounted within a housing adjacent the proximal end of the body 15.

A drill guide shaft 30 extends axially in between the two chambers 35, 36 containing the plungers 20, 21. Preferably, drill guide shaft 30 is disposed approximately equidistant from the longitudinal axis of each of chambers 35, 36 so that when each of the probes 25, 26 is in contact with a bone, the axis of drill guide shaft 30 will be spaced well away from the edge of the bone. In addition, in the illustrated embodiment, the axis of shaft 30 is offset laterally from the plane connecting the axes of chambers 35 so that the axes of the two probes and the drill guide shaft 30 are disposed on vertices of a triangle. See FIG. 2. This configuration facilitates the use of a slot 31 extending the length of guide shaft 30 for receiving a suture during the installation of the suture anchor.

Drill guide shaft 30 is optionally surrounded by an elongate tubular bushing 80 extending throughout at least a portion of the body 15, and preferably positioned so that the distal end of the bushing 80 is slightly recessed from the distal portion 37 of body 15. This bushing 80 aids in properly centering a later installed drill bit and acts as a channel through which a suture anchor is introduced into the hole after drilling.

Referring to FIG. 3, there is disclosed a handle 90 connected to the outside of the body 15 for maneuvering the drill guide 10. This handle 90 is preferably generally tubular in shape, and approximately 10 mm in diameter for easy gripping by the user. The handle 90 as illustrated extends from its connection with the body 15 laterally away from said body, then upward and outward at an angle, and finally ends in a gripping section 91 which extends generally along a perpendicular to the axis of the body 15. This handle design permits the user to forcefully press the drill guide 10 against the body, as well as to facilitate controlled translation of the drill guide along a sagittal axis.

The handle 90 may be connected to the body 15 in any of a variety of conventional manners. In the illustrated embodiment, the handle extends into a small recess in the body 15 and then is locked in place such as with a nut 85. The nut 85 as illustrated has a threaded portion for engaging the body, and a locking portion for pushing the handle 90 into the body 15. Alternatively, the handle 90 can conveniently be integrally molded with body 15, or secured thereto such as by thermal or solvent bonding techniques or by adhesives well known in the art.

It is preferred that the components of the drill guide 10 be made of a material which is sterilizable, relatively rigid and biocompatible, such as stainless steel or any of a variety of polymers conventionally used for medical instruments of the type designed to enter the sterile field.

The operation of the surgical drill guide 10 will now be described. When it is desired to locate a bone for attachment of a suture anchor therein, the drill guide is placed on the body over the area of the bone. The drill guide 10 is centered after visualization or digital palpation over the bone.

The user pushes one or both of the knobs 46 to distally extend at least a first probe 25. The probe 25 is extended into the body by pushing the plunger 20 down, until either the plunger has been fully extended or the bone is contacted.

If the plunger extends fully without the probe contacting the bone, the probe is retracted and drill guide 10 is then repositioned for another attempt at locating the bone.

When the first probe 25 does engage the bone, pressure is released from the knob 46. The user then extends the second probe 26 by pushing on the corresponding knob of the second plunger 20. Once again, the second probe 26 will either engage the bone or the plunger 20 will fully extend without contact. If no contact is made by the second probe 26, both probes 25, 26 are retracted again by pulling upward on the appropriate knob. The drill guide 10 may then be translated along the sagittal axis and one or both probes reextended.

This process is continued until both probes 25, 26 contact the bone and are at approximately equal heights above the body of the drill guide. At this time, the user will be assured that the bone has been located and that the guide shaft 30 is properly centered over the bone.

A drill bit is then extended through the drill bushing 80 and into the patient. The drill bit is used to drill through adjacent tissue and produce a small hole in the bone. Preferably, a step drill or other limiting structure is utilized for producing a hole having a predetermined and reproducible depth into the bone. For installation of the preferred Mitek G2 anchors disclosed herein, a 2.5 mm diameter drill bit is used to produce a hole of 15 mm depth into the bone.

The desirability of having a tissue compression portion 37 which extends distally slightly beyond the distal end of the adjacent body is now apparent. At the time the drill bit is retracted, the hole drilled would normally close upon itself because of the resiliency of the surrounding tissue. However, by maintaining pressure on the body 15 in the direction of the bone, the tissue compression portion 37 tends to compress the adjacent tissue thereby minimizing migration and maintaining the hole open.

In this manner, the tissue located directly under the guide shaft is prevented from closing, and the anchor can be readily advanced through guide shaft 30 and into the bone. Even without distally extending tissue compression portion 37, installation of the anchor is greatly simplified using the drill guide of the present invention because the axis of drill guide shaft 30 remains directed at the drill hole.

Following retraction of the drill bit, a suture anchor is advanced into the body through the drill bushing 80 and then connected within the hole in the bone. An installation tool which facilitates holding the anchor body by means of an interference fit at the gripping point and guiding said anchor through the guide hole and compressed tissue into the bone hole is preferably utilized. The suture, typically previously connected to the anchor, is permitted to trail out through the slot 31 provided for that purpose.

Referring to FIGS. 5–9, there is shown an alternative embodiment of a drill guide for use in locating drill sites inside a patient's body. As illustrated, the drill guide 110 comprises a body 115 carrying one or more probes 125, 126. A drill guide bore 130 is preferably located between the bone probes 125, 126.

The body 115 is the support structure for the drill guide 110. The body 115 may have any of a variety of exterior configurations; however, it is preferred that the body be sufficiently axially elongated to facilitate withdrawal of the sharp distal tips 127, 128 of the probes 125, 126 therein to minimize accidental needle sticks. Body 115 is generally oval or rectangular in cross section.

Figure 6:
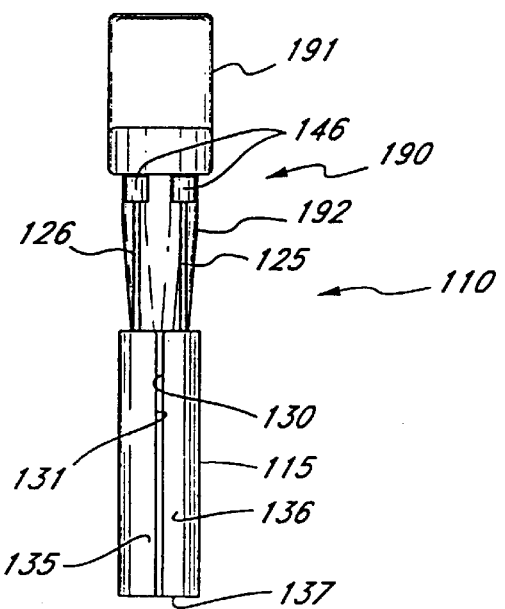
FIG. 6 is a front elevational view of the drill guide of FIG. 5.

Body 115 is provided with one or more bores 135, 136 extending therethrough (FIG. 6). As illustrated, the bores 135, 136 are spaced apart from each other to accommodate a drill guide bore 130. It is contemplated that the drill guide bore 130 may coincidentally be one of the bores 135, 136, in which case the spacing between bores 135, 136 can be reduced. If only one probe 125 is used, there may only be one bore 135, and this bore 135 may coincidentally be the drill guide bore 130 also.

Preferably, the distal end 137 of the body 115 is provided with a number of serrations 134 (FIGS. 8 and 9). In the illustrated embodiment, serrations 134 are located approximately 1 mm apart and run generally parallel to the longest dimension longitudinally across the face of distal end 137. The serrations 134 are sharp ridges formed between curved grooves which have a diameter of about 0.5 mm and extend into the face of the distal end 137.

The exact distance between the axes of the adjacent bores 135, 136 depends on the procedure for which the device is to be used. As illustrated in FIG. 9 and as used in a bladder neck suspension technique, the axes of the bores 135, 136 should be separated by a distance of no more than about 9 mm between centerlines. In this manner, the corresponding probe separation in a two probe embodiment is also no more than about 9 mm. While this is the preferred separation distance, it is also possible for the separation to be anywhere within the range of between about 5 mm and about 10 mm.

Each probe 125, 126 preferably comprises a unitary element such as a wire or needle. An engaging knob 146 is mounted to the proximal end of each probe 125, 126. Knob 146 is a generally cylindrical body which is shaped for easy engagement with a thumb or hand. Knob 146 may be attached to the probes 125, 126 in any of a variety of manners well known in the art. As illustrated, the knob 146 is stainless steel, but may be molded from a thermoplastic material, and provided with a recess for receiving the top of the corresponding probe 125, 126.

The probes 125, 126 extend distally from each knob 146 and into the body 115 through the bores 135, 136. The probes 125, 126 are preferably at least approximately 75 mm long from the distal surface of the knobs 146 to their tips 127, 128. In addition, the axial length of the body 115 is within the range of from about 50 mm to about 60 mm long, and preferably about 50 mm long. The probes 125, 126 thus have a sufficient range of axial travel between a first retracted position in which the distal tips 127, 128 of the probes 125, 126 are shielded inside the bores 135, 136, and a second extended position in which the distal tips of the probes are exposed. It is contemplated, however, that the length of the probes 125, 126 and axial travel may vary depending on the intended procedure.

The knobs 146 act as limits on distal travel of the probes 125, 126, by engagement with the proximal surface of the end wall 140 of the body 115.

The length of the bores 135, 136 is preferably such that the distal tips 127, 128 of the probes 125, 126 are spaced by at least about 3 mm from the open distal end of the bores 135, 136 at the distal end 137 of the body 115 when the probes are retracted. In this manner the probe end is protected against damage, and the patient and user of the drill guide 110 are protected against accidental probe sticks.

Probes 125, 126 are preferably provided with a means for providing a bias in the proximal direction, to releasably retain the probes in the retracted state when not in use. In addition, sufficiently strong biasing means can assist in retraction of the probe from body tissue. The bias may be provided in any of a variety of ways known in the art such as with the use of coil springs. Preferably, a tapered conical section (not shown) is provided on the body of the probes 125, 126. A matching tapered step (not shown) is provided in each bore 135, 136. The conical section and step are arranged to engage each other so that the probes 125, 126 are maintained in a retracted state during non-use because of friction. The probes 125 and 126 may easily be released upon light finger pressure on the knobs 146. Alternatively, any of a variety of releasable retention structures for opposing a bias may be utilized as will be apparent to one of skill in the art.

Figure 5:
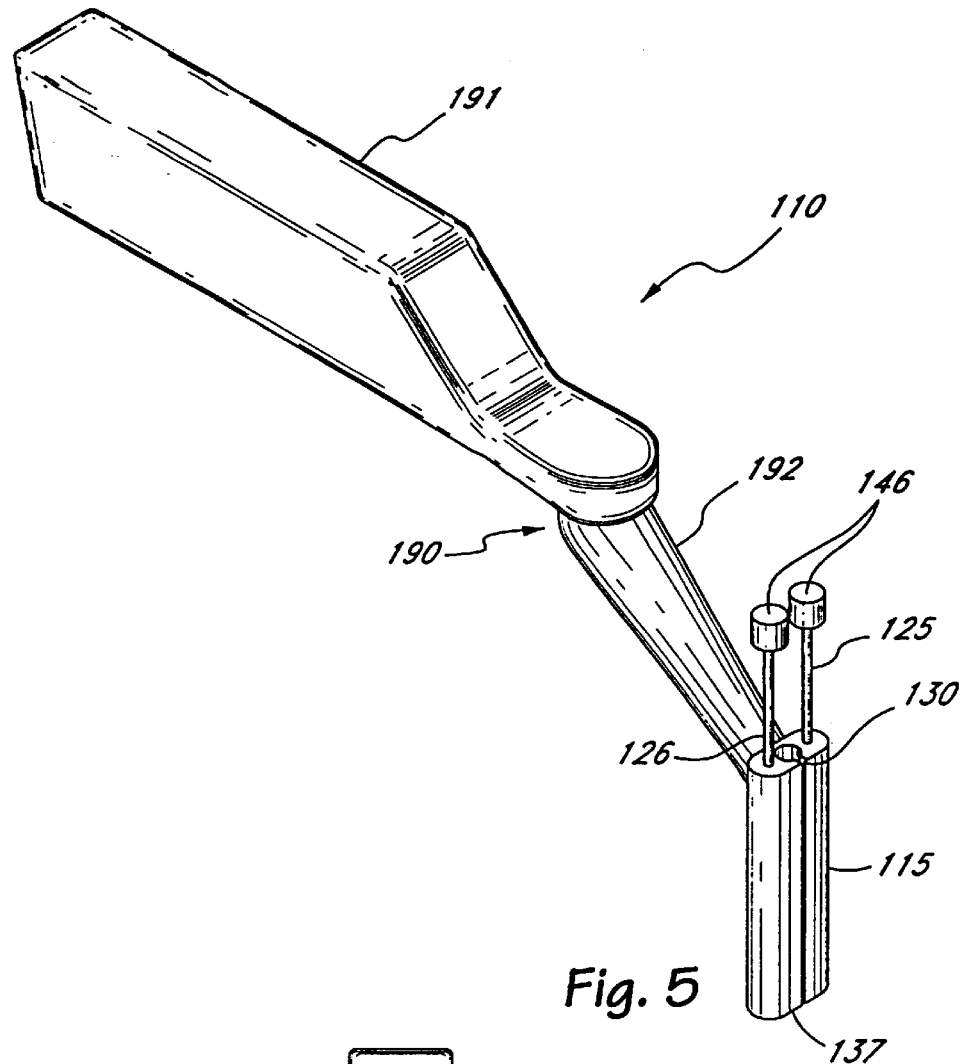
FIG. 5 is a perspective view of an alternate embodiment drill guide of the present invention.

As illustrated in FIGS. 5, 6 and 9 a drill guide bore 130 extends axially in between the bores 135, 136 which contain the probes 125, 126. Drill guide bore 130 in the illustrated embodiment is essentially coplanar with bores 135, 136. However, depending upon the desired diameter of drill guide bore 130 and spacing of bores 135, 136, drill guide bore 130 can be offset from the plane of bores 135 and 136. In general, the minimum diameter of drill guide bore 130 is set by the desired drill bit size and by the desired bone anchor, as has been previously discussed. Typical bone anchors of the type used herein are on the order of 2 mm in diameter.

Preferably, the drill guide bore 130 is disposed approximately equidistant from the longitudinal axis of each of the bores 135, 136 so that when each of the probes 125, 126 is in contact with a bone, the axis of the drill guide bore 130 will be spaced well away from the edge of the bone. In addition, the drill guide bore 130 preferably has a slot 131 extending the length of the guide bore 130 for receiving a suture, and for removing the drill guide after an anchor and suture have been installed.

As illustrated in FIG. 7, a handle 190 is connected to the outside of the body 115 for maneuvering the drill guide 110. The handle 190 preferably comprises two sections: a gripping portion 191 and an attachment portion 192. The attachment portion 192 extends from its connection with the body 115 upward at an angle of about 45 degrees to its connection with the gripping portion 191 which extends generally along a line perpendicular to the axis of the body 115.

The attachment portion 192 can be connected to the body 115 in any of a variety of conventional manners. In the illustrated embodiment, the attachment portion 192 is brazed to the outside of the body 115. The attachment portion 192 could alternatively be integrally molded with the body 115, or it could be otherwise secured to the body 115 by conventional welding, solvent, thermal or adhesive bonding techniques, or fastened with screws or the like.

The gripping portion 191 is preferably approximately 140 mm in length and about 20 mm wide. The gripping portion is about 30 mm thick throughout most of its length, however, near its connection with the attachment portion 191 it tapers at approximately a 45° angle to a thin section of 10 mm thickness and 30 mm length which acts as a thumb rest for the user.

The gripping portion 191 is preferably rotatable about an axis which is perpendicular to the axis of the probes 125, 126. The gripping portion 191 is thus, as illustrated, mounted on a pin 193 which extends from the bottom surface of the attachment portion 192 into a matching hole in the gripping portion 191 and clamped with a centrally located screw.

It is preferred that the components of the drill guide 110 as embodied be made of a material which is sterilizable, relatively rigid and biocompatible, such as stainless steel or any of a variety of polymers conventionally used for medical instruments of the type designed to enter the sterile field.

The operation of drill guide 110 is the same as that described for the embodiment illustrated in FIGS. 1–4. Operation of the single probe embodiment (not illustrated), will be apparent to one of skill in the art in view of the disclosure herein.

If the drill guide 110 has only one probe, the guide is pressed firmly against the tissue in the area over where the bone is believed to be located. The probe 125 is pressed into the body with the knob 146. If the probe 125 does not contact bone firmly, the guide 110 is moved and the probe is re-inserted. Once contact has been established, the probe 125 may be removed from the bore 135 and the drill bit is preferably inserted through the same bore for drilling the hole. Once drilled, pressure is maintained on the drill guide 110 in the distal direction. Tissue will be restrained from occluding the hole by the serrations 134 located on the distal end 137 of the body 115.

Referring to FIGS. 10–14 there is shown yet another alternate embodiment of a drill guide for use in locating drill sites inside a patient's body. This drill guide 210 is similar to that described above, except that this drill guide 210 is designed to be disposable, having a design which is easy to manufacture, and yet fully functional. As illustrated, the drill guide 210 comprises a body 215 carrying one or more probes 225, 226. A drill guide bore 230 is preferably located between the bone probes 225, 226.

The body 215 is the support structure for the drill guide 210. The body 215 may have any of a variety of exterior configurations; however, once again it is preferred that the body be sufficiently axially elongated to facilitate withdrawal of the sharp distal tips 227, 228 of the probes 225, 226 therein to minimize accidental needle sticks. Body 215 is preferably oval or elliptical in cross section preferably being about 7.5 mm wide and 14 mm long on its bottom surface.

Body 215 is provided with one or more bores 235, 236 extending therethrough. As illustrated, the bores 235, 236 are spaced apart from each other to accommodate a drill guide bore 230. It is contemplated that the drill guide bore 230 may coincidentally be one of the bores 235, 236, in which case the spacing between bores 235, 236 can be reduced. If only one probe 225 is used, there may only be one bore 235, and this bore 235 may coincidentally be the drill guide bore 230 also.

Figure 11:
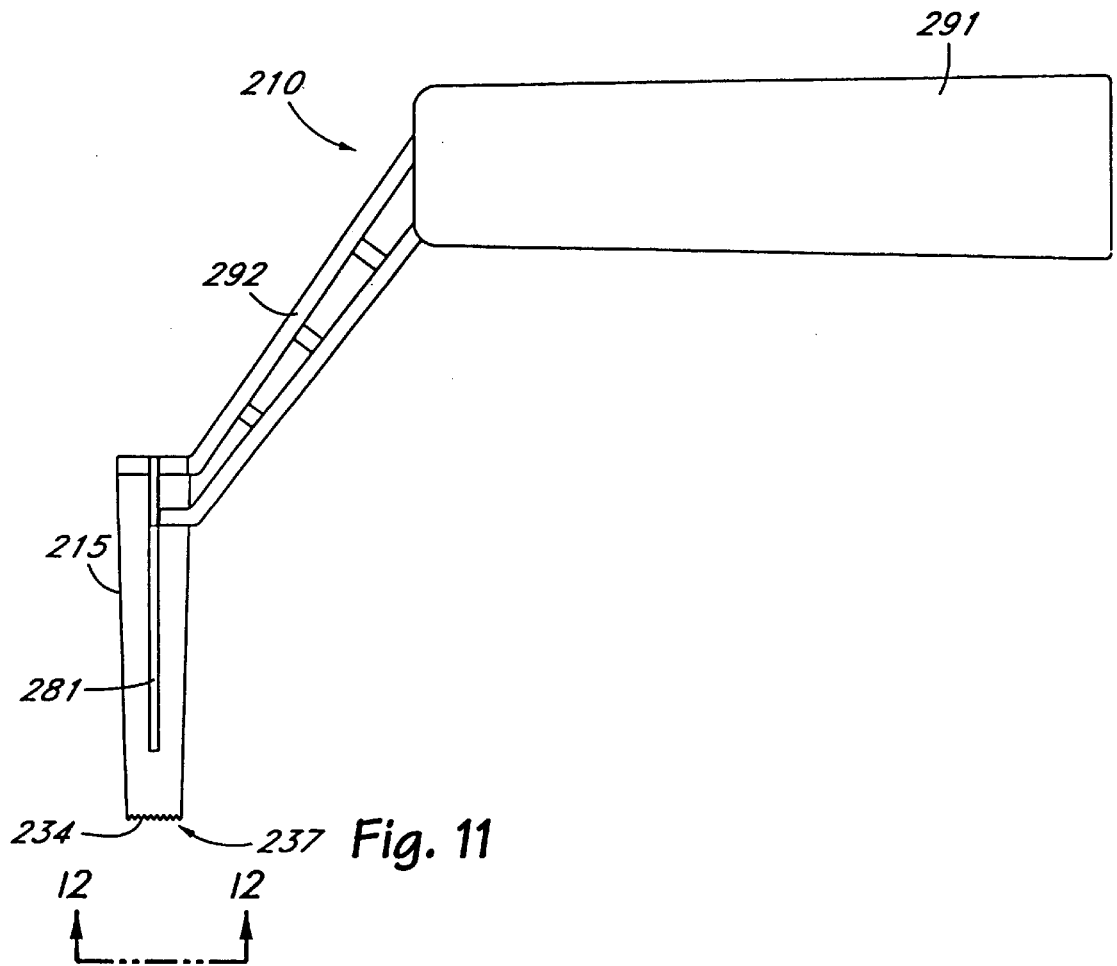
FIG. 11 is a side view of the drill guide illustrated in FIG. 10.
Figure 12:
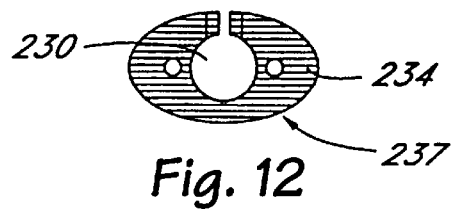
FIG. 12 is an enlarged end view of the drill guide illustrated in FIG. 11.

Preferably, the distal end 237 of the body 215 is provided with a number of serrations 234 (FIGS. 11 and 12). In the illustrated embodiment, serrations 234 are located approximately 1 mm apart and run generally parallel to the longest dimension longitudinally across the face of distal end 237. The serrations 234 are sharp ridges formed between curved grooves which have a diameter of about 0.5 mm and extend into the face of the distal end 237.

Figure 10:
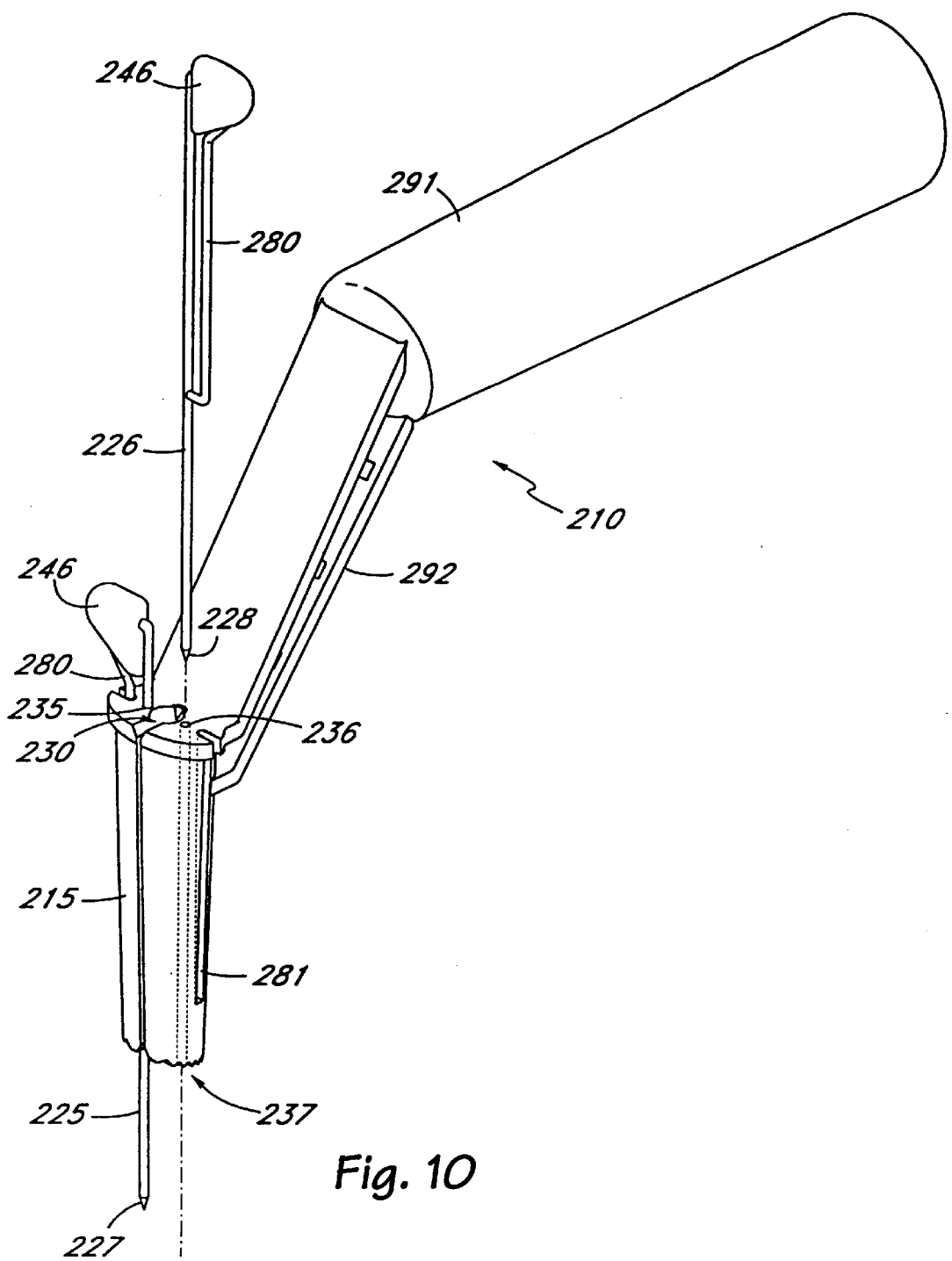
FIG. 10 is a perspective view of an alternate embodiment drill guide of the present invention.

As set forth above, the exact distance between the axes of the adjacent bores 235, 236 depends on the procedure for which the device is to be used. As illustrated in FIG. 10 and as used in a bladder neck suspension technique, the axes of the bores 235, 236 are separated by a distance of about 7 mm between centerlines. In this manner, the corresponding probe separation in a two probe embodiment is also no more than about 7 mm. While this is the preferred separation distance for this embodiment, as discussed above, it is possible for the separation to be anywhere within the range of between about 5 mm and about 10 mm.

As best illustrated in FIG. 10, each probe 225, 226 preferably comprises a unitary element such as a wire or needle. An engaging knob 246 is located at the proximal end of each probe 225, 226. Knob 246 is a generally disc shaped body which is designed for easy engagement with a thumb or fingers. Knob 246 may be attached to the probes 225, 226 in any of a variety of manners well known in the art. As illustrated, the knob 246 is manufactured of a thermoplastic material, and provided with a recess and located about the curved top end of the corresponding probe 225, 226.

The probes 225, 226 extend distally from each knob 246 and into the body 215 through the bores 235, 236. As stated above, the probes 225, 226 are preferably at least approximately 75 mm long from the distal surface of the knobs 246 to their tips 227, 228. In addition, the axial length of the body 215 is within the range of from about 50 mm to about 60 mm long, and in this embodiment is preferably about 50 mm long. The probes 225, 226 thus have a sufficient range of axial travel between a first retracted position in which the distal tips 227, 228 of the probes 225, 226 are shielded inside the bores 235, 236, and a second extended position in which the distal tips of the probes are exposed. It is contemplated, however, that the length of the probes 225, 226 and axial travel may vary depending on the intended procedure.

Guide members 280 also engage the knobs 246 and act to limit the distal travel of the probes 225, 226 and prevent twisting of the knobs 246. The guide members 280 are rigid members which each travel in slots 281 located along the outside of the body 215 which are connected to each corresponding bore 235, 236. The members 280 have a length which, when coupled with the slots 281 is such that when the members 280 engage the end of the slots 281 to limit the travel of the probes 225, 226 the probes have extended out of the body 215 a sufficient distance to allow bone location. As illustrated, the members 280 are formed integrally with the probes 225, 226 as one piece, the probes 225, 226 circling back through the knob 246 and running parallel thereto for a distance, until connecting back to each probe 225, 226.

The length of the bores 235, 236 is again preferably such that the distal tips 227, 228 of the probes 225, 226 are spaced by at least about 3 mm from the open distal end of the bores 235, 236 at the distal end 237 of the body 215 when the probes are retracted. In this manner the probe end is protected against damage, and the patient and user of the drill guide 210 are protected against accidental probe sticks.

Probes 225, 226 may be provided with a means for providing a bias in the proximal direction, to releasably retain the probes in the retracted state when not in use. In addition, sufficiently strong biasing means can assist in retraction of the probe from body tissue. The bias may be provided in any of a variety of ways known in the art such as with the use of coil springs. Alternatively, any of a variety of releasable retention structures for opposing a bias may be utilized as will be apparent to one of skill in the art.

Figure 13:
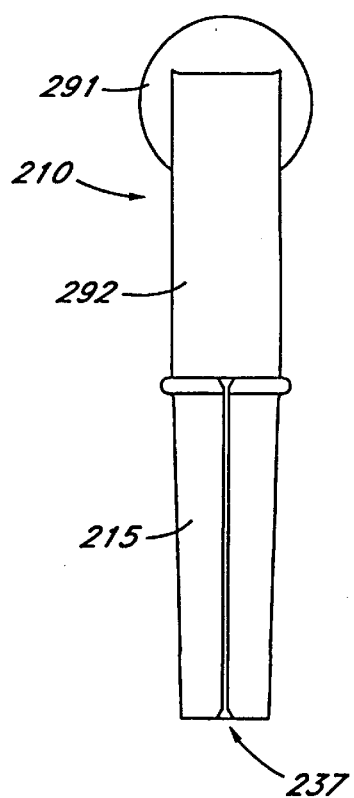
FIG. 13 is a front view of the drill guide illustrated in FIG. 10.
Figure 14:
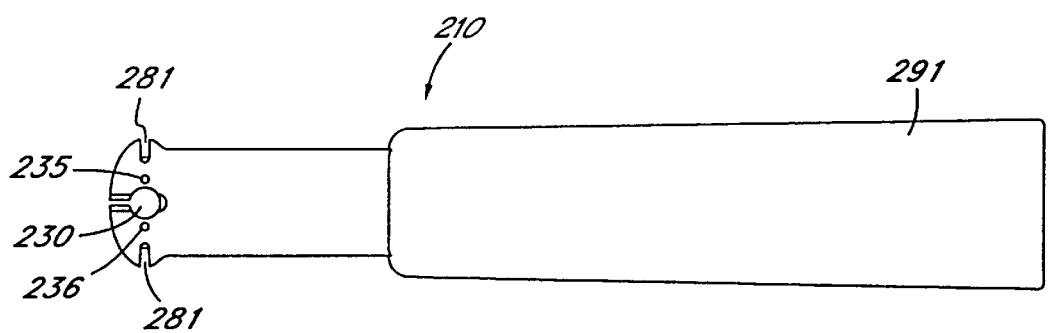
FIG. 14 is a top view of the drill guide illustrated in FIG. 10.

As illustrated in FIGS. 10 and 13 a drill guide bore 230 extends axially in between the bores 235, 236 which contain the probes 225, 226. Drill guide bore 230 in the illustrated embodiment is essentially coplanar with bores 235, 236. However, depending upon the desired diameter of drill guide bore 230 and spacing of bores 235, 236, drill guide bore 230 can be offset from the plane of bores 235 and 236. In general, the minimum diameter of drill guide bore 230 is set by the desired drill bit size and by the desired bone anchor, as has been previously discussed. Typical bone anchors of the type used herein are on the order of 2 mm in diameter.

Preferably, the drill guide bore 230 is disposed approximately equidistant from the longitudinal axis of each of the bores 235, 236 so that when each of the probes 225, 226 is in contact with a bone, the axis of the drill guide bore 230 will be spaced well away from the edge of the bone. In addition, the drill guide bore 230 preferably has a slot 231 extending the length of the guide bore 230 for receiving a suture, and for removing the drill guide after an anchor and suture have been installed.

As best illustrated in FIGS. 10 and 11, a handle 290 is connected to the outside of the body 215 for maneuvering the drill guide 210. The handle 290 preferably comprises two sections: a gripping portion 291 and an attachment portion 292. The attachment portion 292 extends from its connection with the body 215 upward at an angle of about 58 degrees to its connection with the gripping portion 291 which extends generally along a line perpendicular to the axis of the body 215. As illustrated, the attachment portion 291 in preferably molded from thermoplastic, and therefore has a rigid top and bottom support connected by a number of ribs.

The attachment portion 292 can be connected to the body 215 in any of a variety of conventional manners. In the illustrated embodiment, the attachment portion 292 is integrally molded with the body 215 of a thermoplastic, but it could be otherwise secured to the body 215 by conventional welding, solvent, thermal or adhesive bonding techniques, or fastened with screws or the like, depending on the materials used.

The gripping portion 291 of this embodiment is preferably approximately 95 mm in length and primarily cylindrical, having a diameter of about 25 mm. The gripping portion tapers slightly near its connection with the attachment portion 291.

As discussed above with the other embodiment, it is preferred that the components of the drill guide 210 as embodied be made of a material which is sterilizable, relatively rigid and biocompatible. In order for the drill guide 210 to be economically producible for disposable use, it is preferred that the components thereof (excluding the probes 225, 226, which are preferably manufactured of stainless steel) be made of any of a variety of polymers conventionally used for medical instruments of the type designed to enter the sterile field. In particular, the thermoplastic Cycolac GSM 2679F made by General Electric Plastics has been found suitable, which is Acrylonitrile Butadiene Styrene (ABS) material. If it is desired that the drill guide 210 not be disposable, it can be made of stainless steel.

Referring to FIGS. 15–19, there is shown yet another alternate embodiment of a surgical instrument which can be used as a drill guide and/or a bone anchor implantation device, as previously discussed. This bone anchor implantation device is similar to that described above, except for the differences described below and illustrated in FIGS. 15–19.

Figure 17:
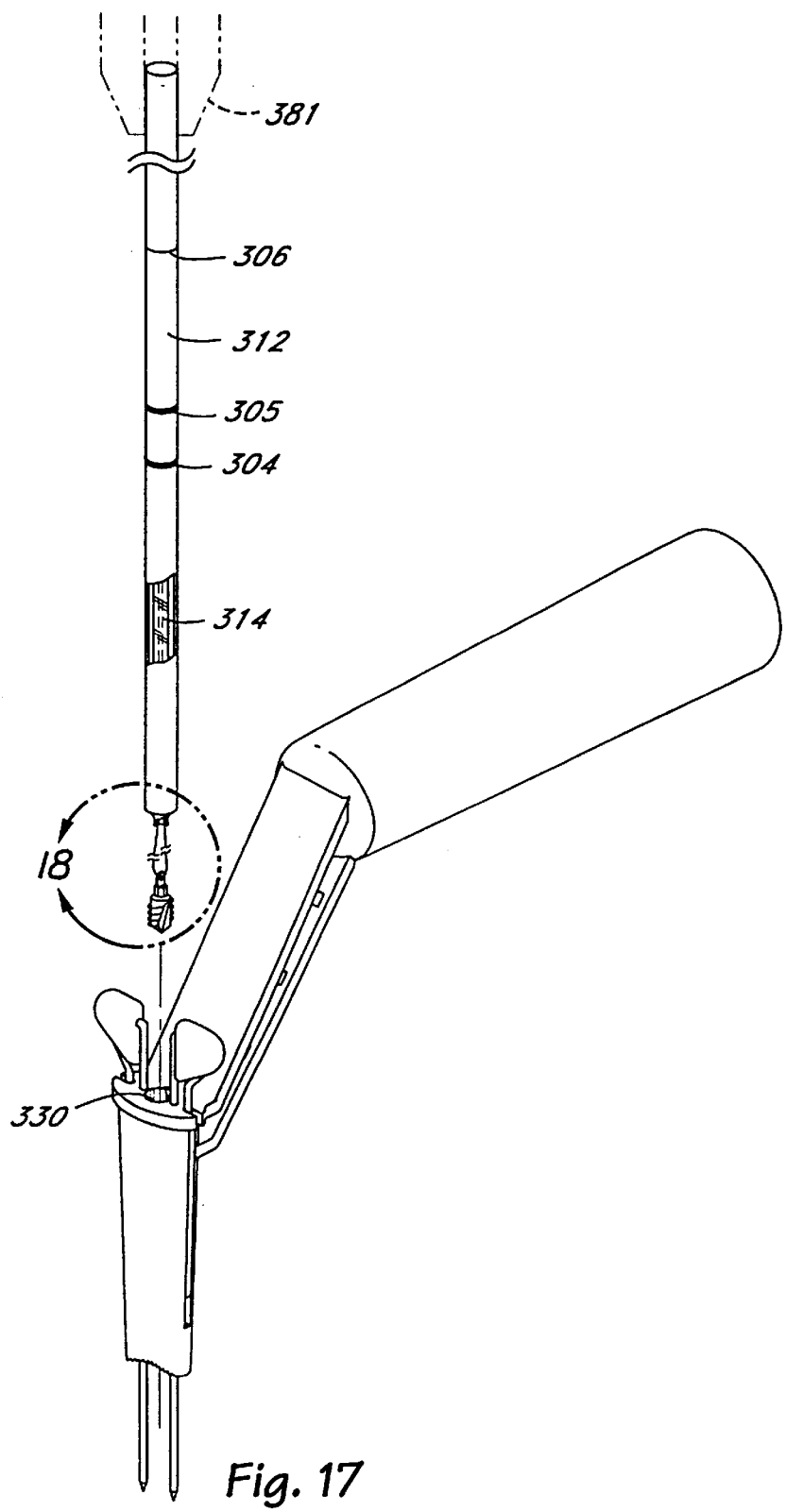
FIG. 17 is an exploded perspective view of the bone anchor implantation device of FIGS. 15 and 16.

As illustrated in FIGS. 15–17, indicia 304, 305, and 306 are included on anchor driver 312. Indicia 304 and 305 provide an indication of the position of anchor 365 relative to bone 375. Indicium 306 provides an indication of a point distally beyond which the drill 381 should not be chucked.

Referring to FIG. 15, when indicium 304 is aligned with the proximal end of each probe 325, 326, then the tip 363 of threaded anchor 365 has passed through soft tissue 374 and is at the surface of bone 375.

FIG. 16 illustrates indicium 305 aligned with the proximal end of each probe 325, 326, which indicates that the distal end 371 of anchor driver 312 is at the surface of bone 375 and that the threaded anchor 365 is fully implanted in bone 375. As will be appreciated by those of skill in the art, the indicium 304, 305 can be located on the driver 312 such that they are intended to align with structures or markings other than the proximal ends of the probes 325, 326 to indicate the position of the bone anchor relative to the surface of the bone. For example, probes 325, 326 can be provided with any of a variety of structures or markings for this purpose. Alternatively, indicium 304 and 305 on driver 312 can be designed for alignment with structures on the body 315, such as the proximal surface of body 315. Preferably, however, the driver 312 is indexed against the probes 325, 326 which most accurately indicate the surface of the bone. The body 315 will normally be separated from the bone by some depth of soft tissue, which may vary from patient to patient, and introduce a degree of uncertainty with respect to the position of the bone anchor 365.

Figure 18:
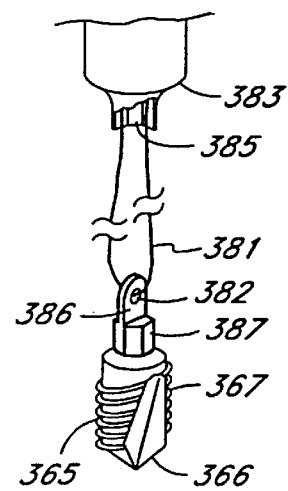
FIG. 18 is an enlarged view of the bone anchor and distal end of the anchor driver of the bone anchor implantation device of FIG. 17.

As illustrated in FIGS. 17 and 18, anchor 365 and suture 381, which is threaded therethrough, are axially releasably but rotationally engaged to anchor driver 312.

FIG. 18 shows an enlarged view of the releasable connection between the proximal end 387 of anchor 365 and the distal end 383 of anchor driver 312. As illustrated in FIG. 18, the distal end 383 of anchor driver 312 is provided with a receiving area 385, which is complementary in shape to the proximal end 387 of threaded anchor 365. The proximal end 387 of threaded anchor 365 can be any of a number of shapes, including regular polygons such as a hexagon as illustrated in FIGS. 17 and 18.

When proximal end 387 of threaded anchor 365 is received within the receiving area 385 of anchor driver 312, the anchor is capable of rotatably penetrating bone when anchor driver 312 is rotated by a tool, such as drill 381. Preferably, bone anchor 365 is in the form of a self tapping screw or drill bit, so that it can be rotatably drilled into the bone, and left in place by axially proximally withdrawing the driver 312. For this purpose, bone anchor 365 is provided with at least one cutting surface 366 and a radially outwardly extending annular flange 367 as will be understood by those of skill in the art.

Preferably, bone anchor 365 is connected to a support element such as suture 381 prior to commencement of a procedure. This may be accomplished in any of a variety of ways, such as advancing suture 381 through an eye 382 in a flange 386 extending proximally from the bone anchor 365. Flange 386 or other attachment structure is optimally dimensioned so that it will not interfere with the complementary nesting of proximal end 387 within the distal end 385 of driver 312.

Preferably, the driver 312 is provided with an axially extending central lumen 314 which opens at its distal end into the receiving area 385. Central lumen 314 is intended to removably receive the suture 381 extending proximally from bone anchor 365 during the drilling and implantation procedure. In this manner, following the rotational implantation of bone anchor 365, the driver 312 is withdrawn proximally to leave suture 381 extending proximally through the tissue from the bone anchor 365.

Although the foregoing embodiments have been described in connection with a rotatably implantable bone anchor 365, it is to be understood the basic methods and apparatus described herein can be readily adapted for use with a bone anchor which is implanted other than through rotational force. For example, any of a variety of bone anchors can be devised for axial distal advancement into a predrilled bore, as will be understood by one of skill in the art. Alternatively, self tapping bone anchors can be devised which rely upon axial compressive force such as that generated by physical impact through the use of hammers, ultrasonic drivers, and the like. All of these variations can be readily adapted by one of skill in the art for use in connection with the present invention.

Figure 19:
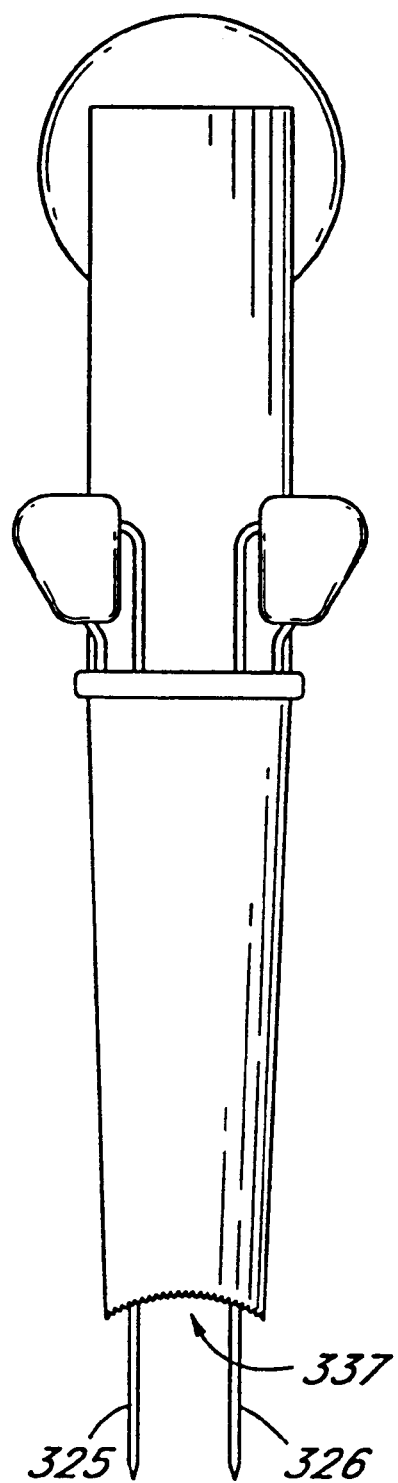
FIG. 19 is a front elevational view of the bone anchor implantation device of FIGS. 15–18.

As illustrated in FIG. 19, serrated tissue compression portion 337 is optimally provided with a concave, contoured surface which is complementary to that of the soft tissue overlying the bone in which the threaded bone anchor is to be placed. In the illustrated embodiment, the curve of the concave surface of tissue compression portion 337 has a depth of approximately 0.070 inches and a radius of curvature of approximately 0.40 inches.

The procedure for positioning the bone anchor implantation device and/or drill guide over a drilling site on bone is the same as that described above.

Having positioned the bone anchor implantation device over a drilling site on bone, a procedure for installing a bone anchor in a bone is generally accomplished as follows. The surgeon attaches anchor driver 312 to a tool, such as a drill 381, capable of rotating anchor driver 312. The drill should be chucked at indicium 306 or at a point proximal thereto.

Anchor driver 312 is inserted in guide channel 330. The surgeon advances anchor driver 312 to a first position at which indicium 304 is aligned with the proximal end of each probe 325, 326. When anchor driver 312 is in the first position, the tip 363 of threaded anchor 365 has passed through soft tissue 374 and is at the surface of bone 375.

The surgeon then further advances anchor driver 312 to a second position at which indicium 305 is aligned with the proximal end of each probe 325, 326. When anchor driver 312 is in a second position, the distal end 371 of anchor driver 312 is at the surface of bone 375 and the threaded anchor 365 is fully implanted in bone 375.

After threaded anchor 365 has been implanted in bone 375, the anchor driver 312 is removed, leaving suture 381 anchored to bone 375. The suture thus anchored, can then be manipulated in any of a variety of surgical procedures such as the bladder neck suspension procedure described in copending U.S. application Ser. No. 08/042,739, filed Apr. 5, 1993 now U.S. Pat. No. 5,611,515, which is incorporated herein by reference.

Although this invention has been described in terms of certain preferred embodiments, other embodiments that are apparent to those of ordinary skill in the art in view of the foregoing are also within the scope of this invention. Accordingly, the scope of the invention is intended to be defined only by reference to the appended claims.

REFERENCES

[1] Pereyra, A. J.: A simplified surgical procedure for the correction of stress incontinence in women. West. J. Surg., 67:223, 1959.

[2] Stamey, T. A.: Endoscopic Suspension of the vesical neck for urinary incontinence in females: Report on 203 consecutive patients. Ann. Surg., 192:465, 1980.

[3] Raz, S.: Modified bladder neck suspension for female stress incontinence. Urology, 17:82, 1981.

[4] Leach, G. E.: Bone fixation technique for transvaginal needle suspension. Urology, 31:388, 1988.

[5] Gittes, R. F. and Loughlin, K. R.: No-incision pubovaginal suspension for stress incontinence. J. Urol. 138:568, 1987.

[6] Winter, C. C.: Peripubic urethropexy for urinary stress incontinence in women. Urology, 20:408, 1982.

[7] McKiel, C. F., Jr., Graf, E. C. and Callahan, D. H.: Marshall-Marchetti procedure: modification. J. Urol., 96:737, 1966.

[8] Hancock, R., Brandstetter, L. H. and Hodgins, T. E.: Transpubic suspension of the bladder neck for urinary incontinence. J. Urol., 123:667, 1980.

[9] Richmond, J. C., Donaldson, W. R., Fu, F. and Harner, C. D.: Modification of the Bankart reconstruction with a suture anchor: report of a new technique. Am. J. Sports Med., 19:343, 1991.

[10] Pederson, B., Tesoro, D., Wertheimer, S. J. and Coraci, M.: Mitek anchor system: a new technique for tenodesis and ligamentous repair of the foot and ankle. J. Foot Surg., 30:48, 1991.

[11] Spencer, J. R., O'Conor, V. J. and Schaeffer, A. J.: A comparison of endoscopic suspension of the vesical neck with suprapubic vesicourethropexy for treatment of stress urinary incontinence. J. Urol., 137:411, 1987.

[12] Araki, T., Takamoto, H., Hara, T. Jujimoto, H., Yoshida, M. and Katayama, Y.: The loop loosening procedure for urination difficulties after Stamey suspension of the vesical neck. J. Urol., 144: 1990.

[13] Webster, G. D. and Kreder, K. J.: Voiding dysfunction following cystourethropexy: Its evaluation and management. J. Urol., 144:1990.

I claim:

1. A method of percutaneously installing a bone anchor in an unexposed bone comprising the steps of:

obtaining a bone anchor implantation device comprising a housing, one or more probes having a proximal portion and a bone contacting tip, and a guide channel;

aligning said guide channel over an unexposed bone by extending said one or more probes until said bone contacting tips of said one or more probes contact said bone;

advancing an anchor driver having a bone anchor releasably engaged thereto through said guide channel to position said bone anchor in said bone; and withdrawing said anchor driver through said guide channel, thereby leaving said anchor in said bone.

2. The method of claim 1, wherein said advancing step comprises advancing said anchor driver until a visual indicia on said driver indicates that the anchor has reached a desired depth in said bone.

3. The method of claim 2, further comprising aligning said visual indicia on said anchor driver with a reference indicia on said one or more probes to indicate the position of said bone anchor relative to the distal end of said one or more probes.

4. The method of claim 1, wherein the step of aligning said guide channel over an unexposed bone comprises aligning said guide channel over a pubic bone.

5. The method of claim 1, wherein said contacting soft tissue overlying said bone with a concave surface on said bone anchor implantation device in order to maintain said soft tissue in an open configuration, thereby reducing tissue migration.

* * * * *